US007000490B1

(12) United States Patent
Micheels

(10) Patent No.: US 7,000,490 B1
(45) Date of Patent: Feb. 21, 2006

(54) THERMOELECTRICALLY COOLED WATER TRAP

(75) Inventor: Ronald H. Micheels, Concord, MA (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 101 days.

(21) Appl. No.: 10/383,624

(22) Filed: Mar. 10, 2003

(51) Int. Cl.
*G01N 1/42* (2006.01)
*G01N 21/15* (2006.01)

(52) U.S. Cl. .................. 73/863.12; 62/3.4; 73/31.07

(58) Field of Classification Search ..........................
73/863.11–863.12, 23.41, 23.42, 31.01, 31.02,
73/31.07; 55/355, 421; 62/3.4
See application file for complete search history.

(56) References Cited

U.S. PATENT DOCUMENTS

| | | | | |
|---|---|---|---|---|
| 4,730,458 A | * | 3/1988 | Alger ........................... 62/3.4 |
| 5,012,052 A | * | 4/1991 | Hayes ........................ 250/288 |
| 5,287,758 A | * | 2/1994 | Geiss et al. ............ 73/863.11 X |
| 5,873,252 A | * | 2/1999 | Springmann .................. 62/3.4 |
| 6,096,178 A | * | 8/2000 | Amirav et al. ................ 62/3.4 |
| 6,101,815 A | * | 8/2000 | van Oort et al. ............... 62/3.4 |
| 6,158,226 A | * | 12/2000 | Noji et al. .................. 62/3.4 X |
| 6,226,994 B1 | * | 5/2001 | Yamada et al. ............... 62/3.7 |
| 6,370,884 B1 | * | 4/2002 | Kelada ........................ 62/3.64 |
| 6,427,449 B1 | * | 8/2002 | Logan et al. .................. 62/3.4 |
| 6,490,879 B1 | * | 12/2002 | Lloyd et al. ............... 62/3.4 X |
| 2001/0042725 A1 | * | 11/2001 | Goodrich .................... 210/801 |

FOREIGN PATENT DOCUMENTS

DE 4102336 A1 * 8/1992
JP 11313849 A * 11/1999

* cited by examiner

*Primary Examiner*—Thomas P. Noland
(74) *Attorney, Agent, or Firm*—Brian J. Lally; Daniel D. Park; Paul A. Gottlieb

(57) ABSTRACT

A water trap system based on a thermoelectric cooling device is employed to remove a major fraction of the water from air samples, prior to analysis of these samples for chemical composition, by a variety of analytical techniques where water vapor interferes with the measurement process. These analytical techniques include infrared spectroscopy, mass spectrometry, ion mobility spectrometry and gas chromatography. The thermoelectric system for trapping water present in air samples can substantially improve detection sensitivity in these analytical techniques when it is necessary to measure trace analytes with concentrations in the ppm (parts per million) or ppb (parts per billion) partial pressure range. The thermoelectric trap design is compact and amenable to use in a portable gas monitoring instrumentation.

27 Claims, 13 Drawing Sheets

THERMOELECTRICALLY COOLED WATER TRAP

U.S. GOVERNMENT RIGHTS

The United States Government has rights in this invention pursuant to Contract No. DE-FG02-96ER82258 between the U.S. Department of Energy and Polestar Technologies, Inc.

TECHNICAL FIELD

The present invention relates to an apparatus for removing water vapor from air. More specifically, the present invention teaches an apparatus for removing water vapor from air samples, prior to analysis of these samples for chemical composition. The present invention can be used in conjunction with a variety of analytic systems including those used for infrared spectroscopy, mass spectrometry, ion mobility spectrometry and gas chromatography. The present invention is particularly well suited for removing water vapor that interferes with the analysis of compounds by mid-infrared absorption spectroscopy.

BACKGROUND OF THE INVENTION

Water vapor interference is a common problem in the analysis of air samples for chemical composition. Water vapor interferes with the analysis of the air samples for trace chemical species by masking the signal(s) for the element(s) or compounds(s) being tested for. Although water vapor interference effects a variety of analytical techniques including mass spectrometry and gas chromatography, it has the greatest impact on mid-infrared spectroscopy of trace analytes.

Water vapor is a particularly bad problem for mid-infrared spectroscopy because water vapor produces strong interfering absorption bands in several regions of the 4,000–400 $cm^{-1}$ (2.5–25 $\mu m$) mid-infrared spectral range. In fact, the two strong water absorption bands located at 4,000–3,000 $cm^{-1}$ and 2,300–1,300 $cm^{-1}$ cloud over 50% of the mid-infrared spectral range making it very difficult to measure trace chemical species in this spectral range.

Water vapor interference becomes more pronounced in humid conditions. At conditions of 80% or higher relative humidity (and 25° C.), the concentration of water vapor is 2.5% or 25,000 ppm by volume (partial pressure). The interference of high concentrations of water vapor is greatest in situations where trace concentrations of chemical species are being measured. This is especially true when one is trying to measure chemical species in the concentration range of 200 ppm–1 ppb.

The problem of water vapor interference is compounded by the use of infrared absorption pathlengths in the range of 1–50 m which are typical when measuring analytes with concentrations of 200 ppm–1 ppb partial pressure. Gas phase analyte commonly measured by mid-infrared spectroscopy with 1–50 m absorption pathlengths for which water vapor produces substantial interference include volatile organic compounds and fossil fuel combustion products such as $NO_2$, NO, $SO_2$ and $NH_3$. At such long pathlengths, water interference can reduce infrared light transmission to less than 10%. Low level of infrared transmission results in large reductions in the signal/noise level of the infrared absorption measurements of gas phase analytes.

One approach to reducing interference from water vapor is to subtract a re-scaled version of a reference water spectrum for only water plus air from the sample absorption spectrum. The theory behind this approach is that removing the reference water/air spectrum will reveal an un-obscured sample spectrum, however, this approach has several significant limitations.

First, the detailed vibrational-rotational structure of water absorption bands are very sensitive to both the partial pressure of the water vapor and the partial pressure of other species present at higher concentrations such as $CO_2$ (typically present at concentrations of around 400 ppm). Therefore, for the subtraction method to work effectively the partial pressure of the water vapor and the other major components in the reference spectrum must match that of the sample spectrum. Differences in the water partial pressure between the sample and reference spectrum results in differences in the spectral widths, height and shape of the water sub-band peak due to the vibration-rotational structure which arise from collisional line broadening effects. When differences in spatial widths, height, and shape of infrared spectral absorption features occur, the subtraction of the reference spectrum can only partially remove the water band interference.

Second, because water vapor is still physically present in the sample, water vapor interference can still reduce infrared light transmission to less than 10% (for 1–50 m absorption pathlengths) in many mid-infrared regions. This loss in light transmission limits the detection sensitivity for trace atmospheric constituents even when the water absorption features can be successfully removed by digital subtraction of a water vapor reference spectrum.

A second approach to reducing water interference is to pass the sample gas through a chemical filter which removes water through a chemical reaction such as a hydration reaction. A common water filter agent using a hydration reaction is anhydrous $MgSO_4$. The primary problem with this approach is that the chemical drying agent will also remove a substantial portion (greater than 30%) of the trace analytes of interest in the air sample.

A third approach for reducing water vapor includes passing the sample gas through the inside of a 1 m or greater length porous Nafion membrane (type of fluro-sulfnonate polymer) tubing while a countercurrent flow of dried nitrogen or dried air is maintained over the outside of the tubing. This approach is not always practical because of the requirement of a pressurized source of water-free nitrogen or air. This approach is particularly impractical for portable measurement systems.

A more successful approach to combating water interference is to use a thermoelectrically cooled cold trap which is cooled to a sufficiently low temperature to remove a large fraction of the water vapor present without removing any significant amount of the trace analytes (analyte(s)=the compound(s) or element(s) in the sample being analyzed) present. Assuming thermal equilibrium has been reached, when water vapor is present at a concentration of about 20,000 ppm (2% by partial pressure) a reduction of 75 fold can theoretically be achieved by cooling the air to a temperature of −28° C. In application, the sample gas passes too rapidly through the cold trap for thermal equilibrium to be reached. Even so, experimental measurements have shown that a reduction in the water vapor of about 5 fold can be achieved with a portable thermoelectric cooling system that has a temperature of −28° C. and a gas flow rate of about 1.5 liter/min. This 5 fold reduction in the water vapor reduces the loss of infrared light by optical absorption from the water bands in a 1 m pathlength gas cell from a 87% loss down to a 28% loss. Substantial reductions in water vapor concentration can still be achieved by passing the sample gas through a thermoelectrically cooled water trap cooled to a temperature of −5° C.

In general, the concentration of the trace components in the air sample are not reduced by the cold trap if the equilibrium vapor pressure of the compound is above their partial pressures in the air sample. The partial pressure of a compound such as a volatile organic compound often needs to be lower than the equilibrium vapor pressure because of the condensation of azeothrophic mixtures between water and the analyte compound. This partial pressure condition is met for many compounds of interest including: benzene, toluene, xylenes, ethylbenzene, trichloroethylene, NO and $NO_2$, when present in the sample at concentrations below 200 ppm.

SUMMARY OF THE INVENTION

An apparatus has been devised for the trapping of water from air samples, prior to analysis of these samples for chemical composition, by a variety of analytical techniques including: infrared spectroscopy, mass spectrometry, ion mobility spectrometry, and gas chromatography. One area of special application is the analysis of air samples for volatile compounds by mid-infrared spectroscopy.

Interference from water vapor absorption can be very strong for a large fraction of the mid-infrared and near infrared spectral region of air samples being analyzed for trace amounts of analytes at the ppm (parts per million) or ppb (parts for billion) concentrations by partial pressure. Typical air samples include: indoor or outdoor atmospheric samples, samples of the headspace gas above soil, water samples, and exhaust stack gas, all of which often contain water at concentrations above 10,000 ppm (or 1%) by partial pressure. Interference from water vapor in the mid-infrared analysis of air for trace concentration of gases can substantially reduce the detection sensitivity for the analyte gases.

The present invention allows for very rapid (less than 5 seconds in some cases of headspace gas analysis with samples contained in 40 m sample vials) removal of a major fraction of the water present without a substantial loss in the analyte compounds.

The invention is based on rapid cooling of sample air passing through a metal tube or channel which is cooled with a thermoelectric (Peltier) cooling device. This technique relies on the increased equilibrium vapor pressures of the analyte compounds relative to water at the cooled trap temperatures and the higher initial partial pressures of water in humid air. The application of this technique involves rapid flow (for example 1–6 liters/min) of the air being analyzed through the cold trap, and trapping of the water in non-equilibrium conditions. A typical application is the analysis of air samples for organic solvents such as benzene, toluene, xylenes, ethylbenzene, or trichloroethylene or inorganic compounds such as NO and $NO_2$. In these later examples, the trap functions effectively when cooled to a temperature of −5 to −30 C.

The trap design is compact and amenable to use in a portable gas monitoring instrument. In one embodiment the thermoelectric water trap was powered with a 12V DC power supply.

Other applications of the present invention include trapping water prior to analysis by mass spectrometry, ion mobility spectrometry, gas chromatography and other measurement devices, where water vapor interferes with analysis.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements

DETAILED DESCRIPTION OF THE PREFERRED EMBODIMENTS

Figure 1:
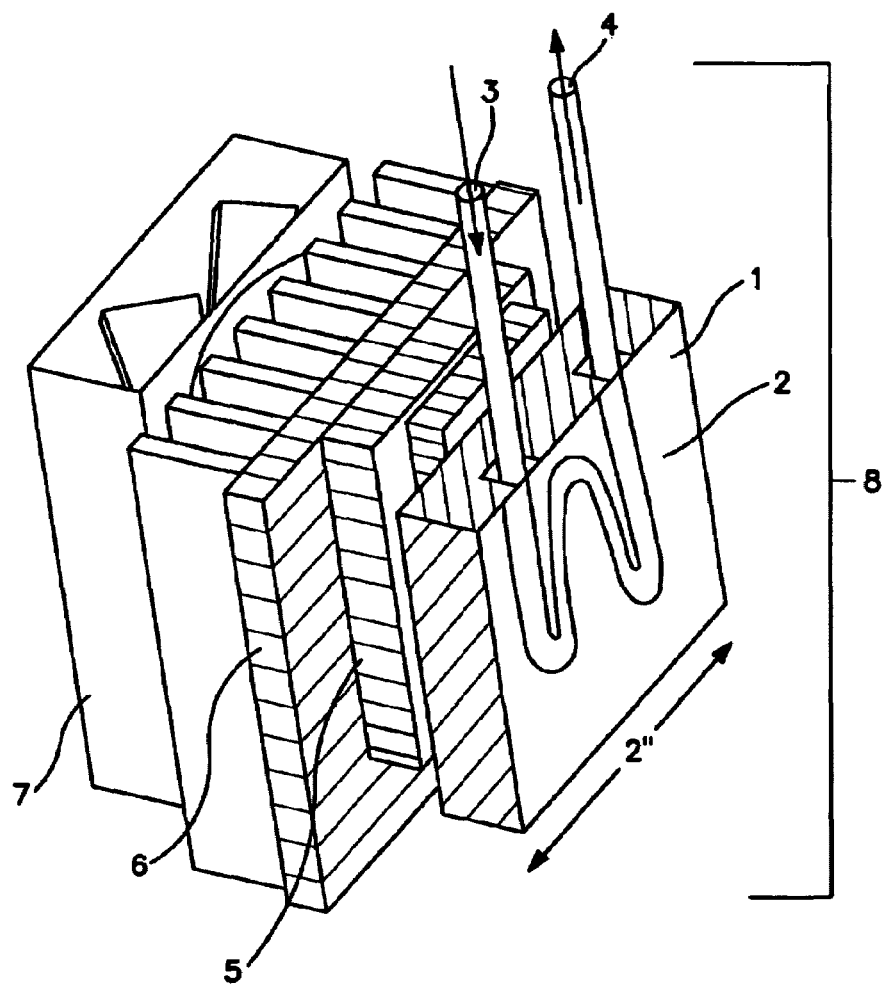
FIG. 1—is a diagram of one embodiment of the present invention, consisting of: copper metal plate containing a heat exchanging gas channel made of metal tubing; a two stage thermoelectric cooler, an aluminum heat sink with radiator fins, and a box fan.

FIG. 1 illustrates a schematic view of an embodiment of the thermoelectrically cooled water trap 8. The first embodiment consists of a metal plate 1, a heat exchanging pipe 2, a two-stage thermoelectric cooler assembly 5, a heat sink with cooling fins 6, and a fan 7.

The metal plate 1 is preferably manufactured out of a good thermal conducting metal such as copper and has a first side, a second side and a top and a bottom. The metal plate 1 has a continuous cavity cut into its second side. In the embodiment as shown, the cavity originates at the top of the plate (inlet end), winds through the central portion of the plate 1, and terminates at the top of the plate (outlet end) as shown in FIG. 1. Other embodiments can be imagined with different inlet and outlet arrangements.

The cavity can be of any shape, but it is preferable to use shapes with bends in them like U's or W's that allows for long pathlengths through the plate (providing more area for heat exchange). Bent shapes like U's or W's also allow for easier collection and removal of water from the trap.

The cavity of the plate 1 is created using machining techniques known in the art or other techniques that would form such a cavity.

The heat exchanging pipe 2 has an inlet end 3 and an outlet end 4. The heat exchanging pipe 2 has a shape that is complimentary to the plate cavity's shape. The pipe 2 fits very snugly in the complimentary cavity of the pipe. The snugness of the fit is important because greater physical contact between the plate and pipe translates into increased efficiency of heat transfer.

The heat exchanging pipe 2 is bonded to the metal plate 1 using a Sb/Sn solder or similar soldering or attachment means. The heat exchanging pipe 2 is preferably made of a good thermal conducting material such as copper.

The inlet 3 and outlet 4 ends of the heat exchanging pipe 2 extend out of inlet and outlet apertures of the metal plate 1 as shown in FIG. 1. The inlet 3 and out let 4 ends of the pipe extend out of the plate a sufficient distance to allow connection of the ends to an analytic system. (details of system attachment to be discussed in detail later in this specification)

The entire length of the heat exchanging pipe 2 (with the exception of the inlet 3 and outlet end 4 extending out of the plate) is in physical contact with the inner surface of the plate's cavity, allowing for transfer of heat (by conduction or other means) between the two surfaces. In the present embodiment the space between the cavity and the heat exchanging pipe is filled with Sb/Sn solder.

Optionally, an insulating piece of polyurethane foam which is formed to fit snuggly around the exact outside shape of the plate and cooler (not shown), covers the plate 2 and the cold side of the thermoelectric cooler 5, and is used to insulate the second end of the plate 2 and cold side of the cooler 5 from the warmer room air surrounding the device.

In an alternate embodiment, a continuous heat exchanging channel can be machined or otherwise formed through the plate 1, the channel performing that same function as the pipe 2. The apparatus would operate similar to the first embodiment, except that the fluid would flow through a channel formed through the plate 1 itself instead of flowing through a pipe.

The two-stage thermoelectric cooler assembly 5 has a "hot" side and a "cold" side. The cooler assembly 5 is a solid state heat pump that operates on the Peltier effect, the theory that there is a heating or cooling effect when electric current (dc) passes through two dissimilar conductors. Typical thermoelectric coolers comprise an array of dissimilar conductors soldered between two ceramic plates, connected electrically in series and thermally in parallel. The conductors are n-type (having more than enough electrons to complete a perfect molecular lattice) and p-type (not having enough electrons to fill a lattice structure), materials. The electrons in the n-type material and holes in the p-type material are called carriers and are the agents that transfer (heat) energy from the "cold" to "hot" side of the assembly as the electrons move from a high to low energy state. Good thermoelectric semiconductor materials impede conventional heat conduction from "hot" to "cold" surfaces, while providing transfer of carriers to move (heat) energy from the cold to hot side of the thermoelectric device. For more information on the Peltier Effect see, *Van Nostrand's Scientific Encyclopedia*, Ninth Edition, Volume 2, pp 3471–72, Wiley-Interscience (2002), which is hereby incorporated by reference in its entirety.

The thermoelectric cooler assembly used 5 in the present case was a two staged thermoelectric cooler manufactured by the Melcor Corporation (Trenton, N.J.) part no. 2 SC 055 045-127-63 (imax.–6 Amp., Qmax–34 Watt) but another thermoelectric cooling assembly 5, with similar properties could also be used.

Both the "hot" and "cold sides" of the cooler assembly 5 are covered with a thin film of thermal interface material (TIM) to enhance thermal conductivity. Although TIMs are excellent thermal conductors, they are not as thermally efficient as metal to metal contact. Therefore, TIMs should be used sparingly to help to fill microscopic surface imperfections in the cooler assembly 5. At the time of the invention thermally conductive aluminum nitride paste was found to be preferable.

The cold side of the cooler assembly 5 is in contact with the first side of the plate 1, allowing for transfer of heat between their respective surfaces. The "cold" side of the cooler assembly 5 and first side of the plate 1 are coupled together by mounting screws or other similar coupling device or material that will not significantly interfere with the thermal conductivity between their respective surfaces.

Heat is transferred from the plate 1 to the "cold" end of the cooler assembly 5, by heat transfer means. Solid phase conduction is the primary heat transfer means. The heat transfer between the plate 1 and assembly 5 cools the plate 1 and reduces its temperature considerably. The desired temperature ranges for the plate 1 are described in detail later in this specification.

Similarly, the heat exchanging pipe 2 (or the heat exchanging cavity in the alternative embodiment) is cooled by conduction (or other heat transfer means) as heat from the pipe moves from the pipe 2, to the plate 1 and then to the "cold" side of the cooler assembly 5.

As explained earlier, the heat absorbed at the "cold" end of the cooler assembly is transferred to "hot" side of the assembly using the Peltier effect.

The "hot" side of the cooler assembly 5 is in physical contact with the first end of the heat sink 6, allowing for heat transfer between their respective surfaces. The cooler assembly 5 and heat sink 6 are coupled together by mounting screws or other similar coupling device or material that will not significantly interfere with the thermal conductivity between their respective surfaces.

The heat sink 6 removes heat from the "hot" side of the cooler assembly 5 primarily by conduction (although other heat transfer means might be at work) The heat sink 6 is made of a metal (preferably aluminum) and has fins which enhance heat removal from the thermoelectric cooling device's 5 second side.

The second end of the heat sink 6 is connected to the first end of the box fan 7 by mounting screws or some similar coupling device or material. The box fan 7 forces air through the fins of the heat sink 6 to augment heat removal from the heat sink 6. In this case a Comair Rotron (San Deigo, Calif.) box fan was used, but another box fan with similar features could also be used.

The heat exchanging tube 2 cools the sample air by removing heat from the air. This heat is in turn removed from the pipe 2 by the chilled plate 1. The "cold" side of the cooler 5 removes the heat from the plate 1 and transfers it to the "hot" side of the cooler assembly 5 (using the Peltier effect). Finally, the heat sink 6 removes the heat from the second side of the cooler assembly 5 and the fan 7 blows ambient air through the fins of the heat sink to help remove the heat more efficiently.

To achieve improved stability in plate temperature, an electronic proportional type temperature controller could be employed. The proportional temperature controller would read the plate temperatured through a temperature sensing device such as a platinum resistance thermometer sensor and would respond to small temperature changes by adjusting the electrical power supplied to the thermoelectric cooler in an appropriate manner to counteract any temperature changes. A suitable controller is an Omega Engineering model CN77323-PV controller with a model RTD-830 platinum resistance thermometer temperature sensor, manufacture by Omega Engineering (Stamford, Conn.).

Before the commencement of air sampling the temperature of the of heat exchanging pipe 2 is preferably lowered to a point below the dew point of the air. It is more preferable that the temperature of the pipe 2 is substantially below the dew point of the air. It was found that a temperature between $-5°$ and $-31°$ C. was a preferable temperature range. It was found that a temperature of between $-5°$ and $-10°$ C. was a even more preferable temperature range. The temperature is important because efficient condensation of water vapor occurs when the temperature of the air is lowered to its dew point or below.

As the sample air flows through the heat exchanging tube 2 it is rapidly cooled to a temperature that is substantially below the dew point of the air and a large fraction of the water vapor condenses (in the form of ice or water droplets) on the walls of the tubing 2 removing substantial amounts of water vapor from the sample air.

Because many gas monitoring applications require a measurement time of less than 2 minutes, the air flow through the water trap 8 must often be rapid enough to pass the entire sample volume through the trap 8 in a period ranging from 1 second to 1 minute. (add flow rate/flow time ranges) As a result of the short flow times required, the gas does not always stay in the water trap 8 long enough to reach thermal equilibrium with the cooled walls of the heat exchanging pipe 2. Despite this fact the present invention is still effective at removing a large percentage of water vapor from air samples as illustrated in the following results.

The present invention can be powered any suitable dc power source. The present embodiment is powered by a 12V DC power source.

Attachment to Analytic Devices and Systems

Figure 4A:
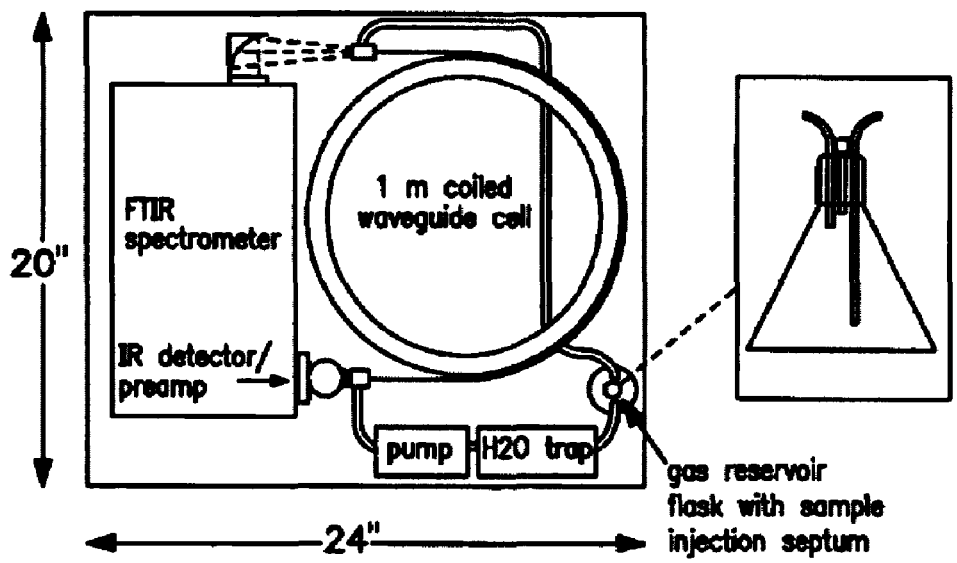
FIGS. 4A—diagram of an experimental system used in evaluating the thermoelectric water trap with samples of humid room air with trace amounts of organic solvents.
Figure 4B:
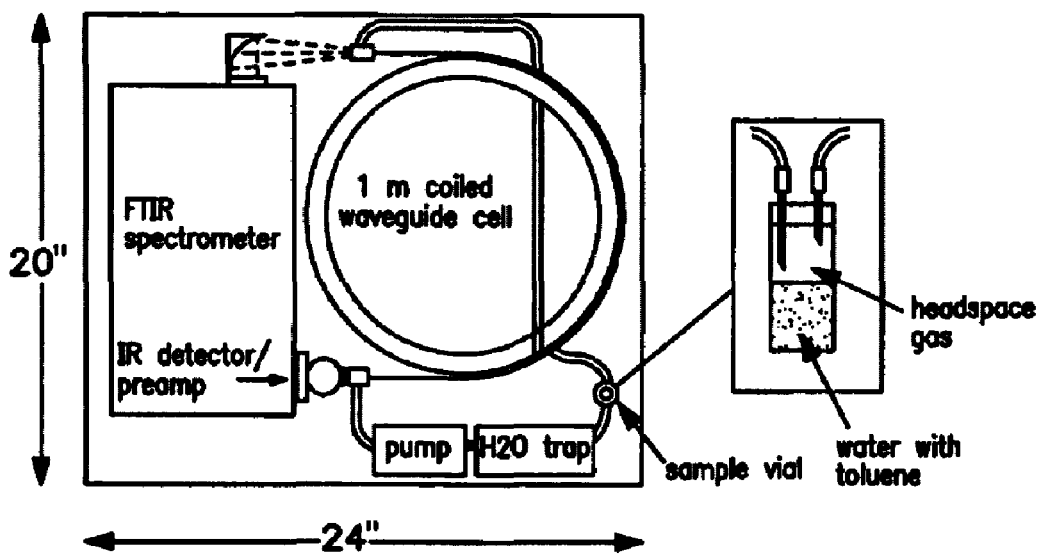
FIGS. 4B—diagram of an experimental system used in evaluating the thermoelectric water trap with headspace gas samples from vials of water with trace amounts of dissolved toluene.
Figure 5:
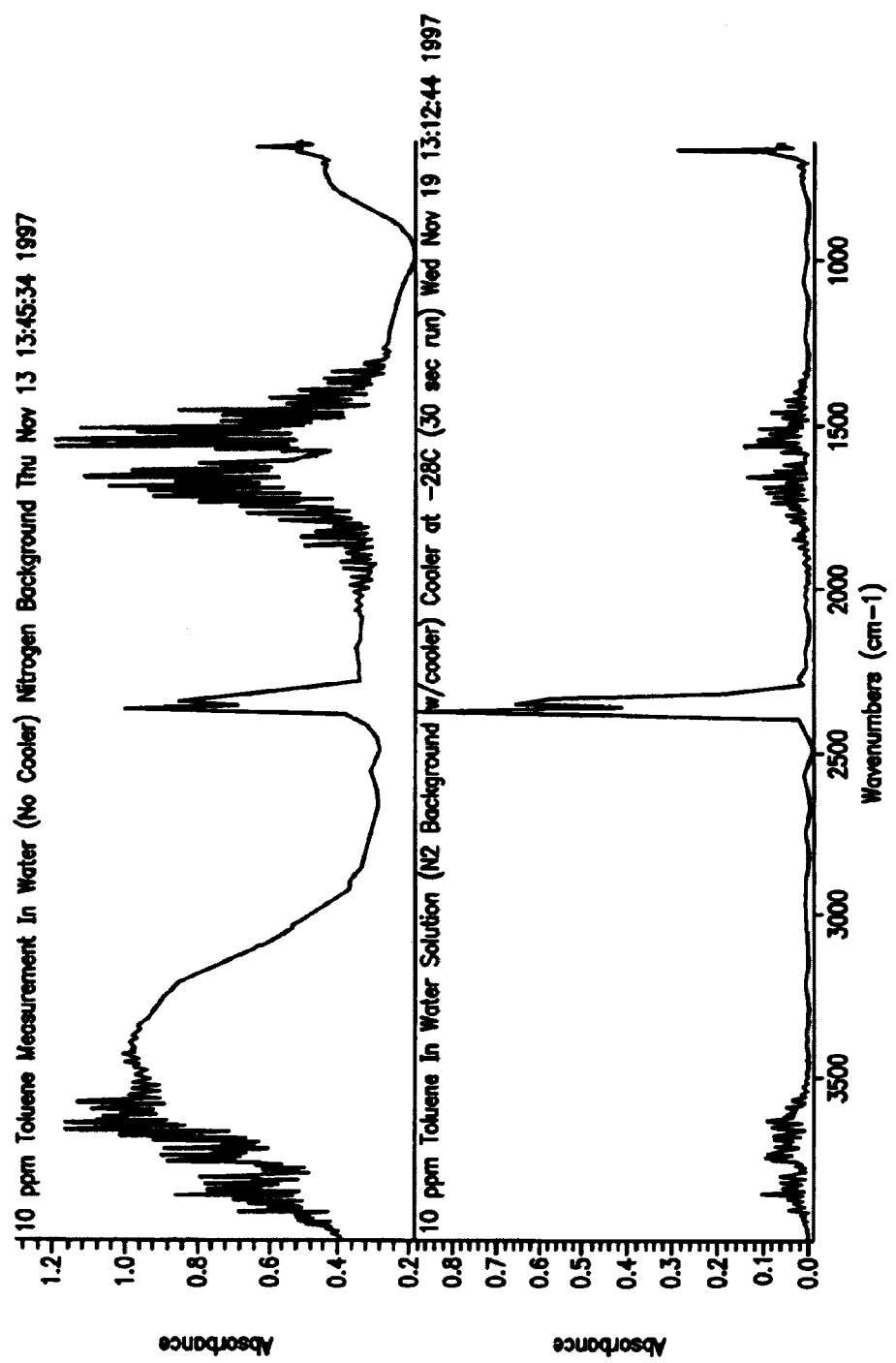
FIG. 5—infrared FTIR spectra of head space above a water sample containing 10 ppm(weight) toluene, both with/without trap, showing complete mid-infrared spectral range.
Figure 6:
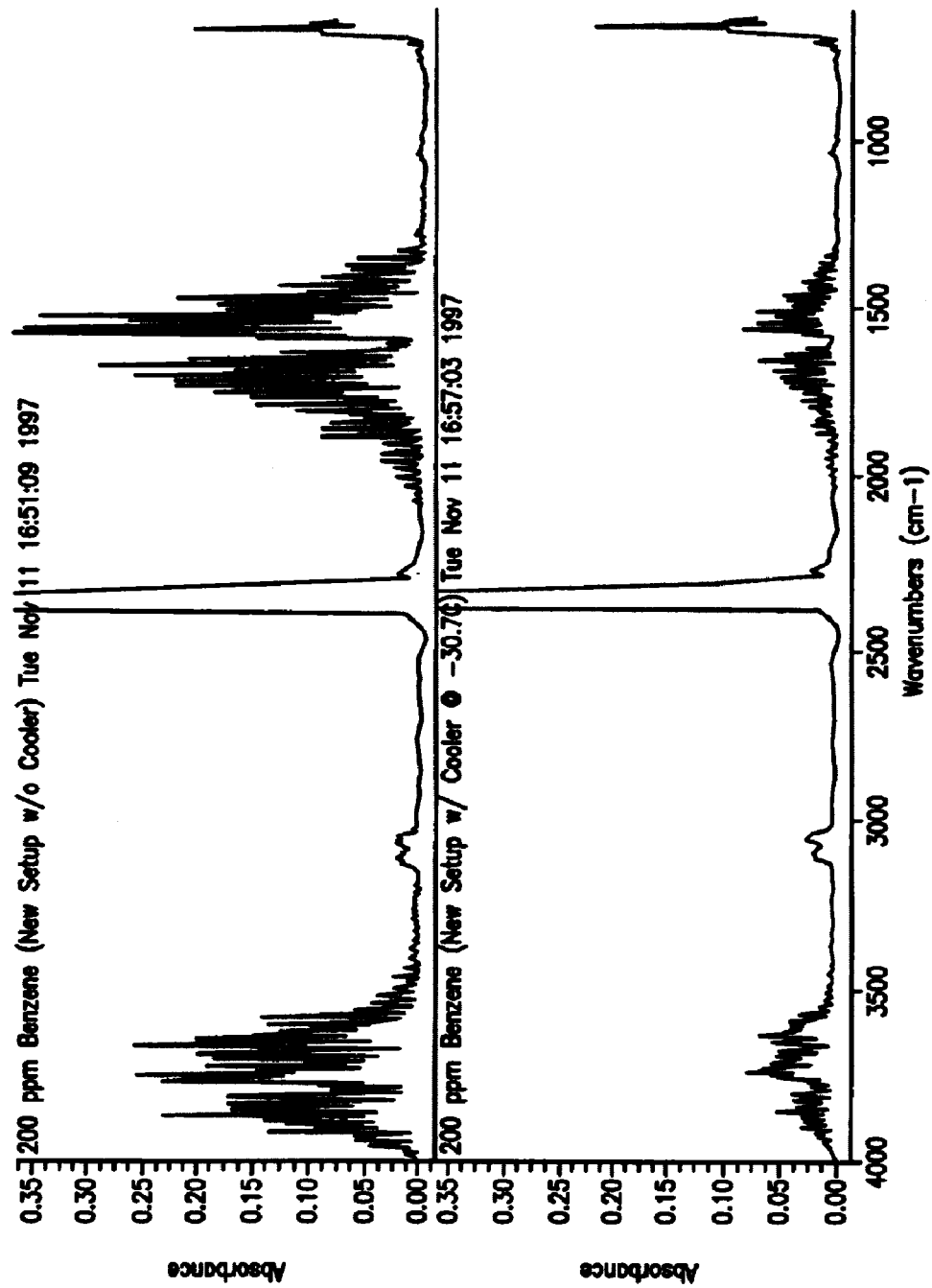
FIG. 6—infrared FTIR spectra for 200 ppm (volume) of benzene in room air (approximately 50% relative humidity), both with/without water trap filtration, showing water vapor reduction without significant organic compound loss. Spectrum shows the complete mid-infrared range.
Figure 7:
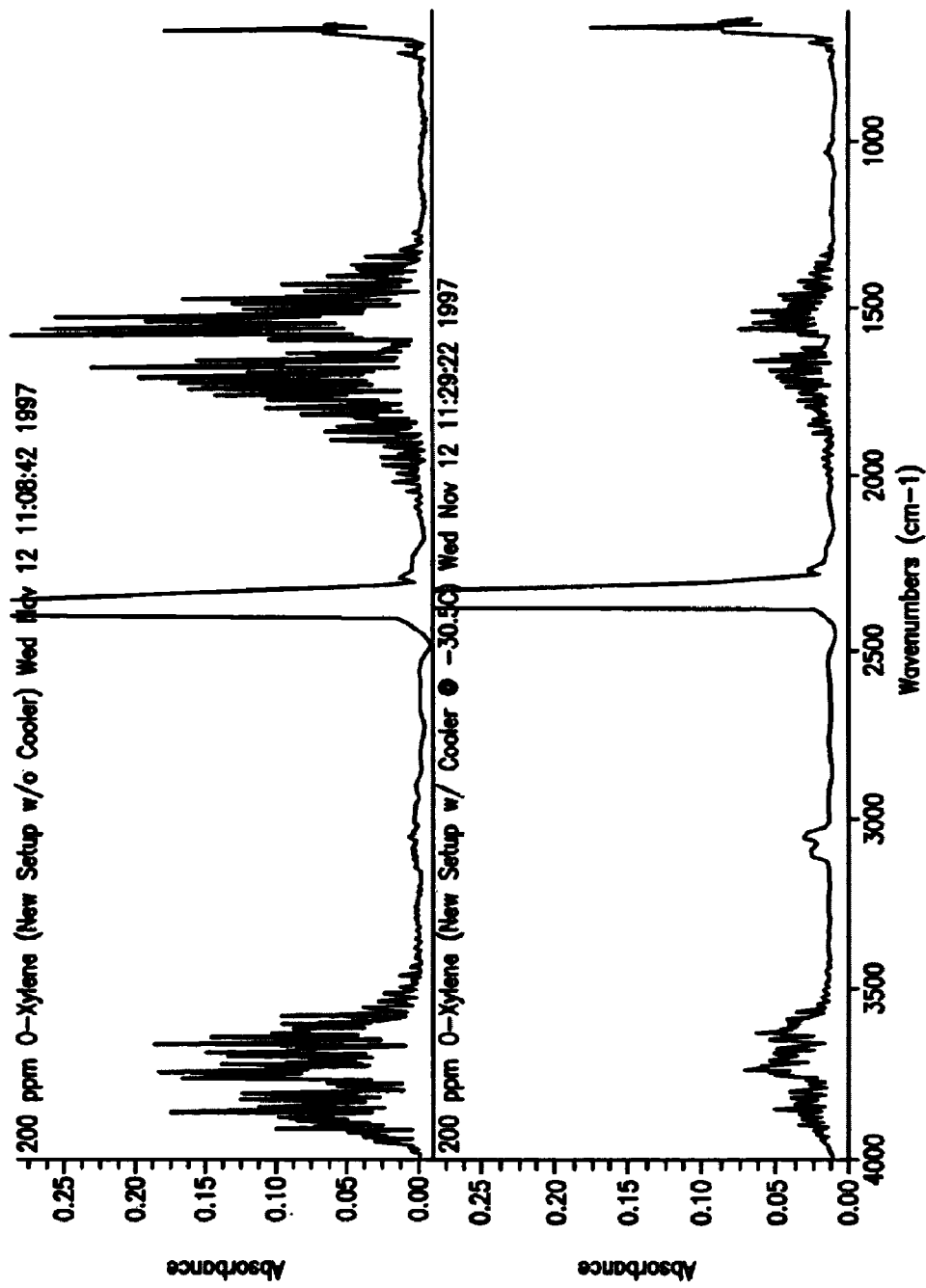
FIG. 7—infrared FTIR spectra for 200 ppm (volume) of o-xylene in room air (approximately 50% relative humidity), both with/without water trap filtration, showing water vapor reduction without significant organic compound loss. Spectrum shows the complete mid-infrared range.
Figure 8:
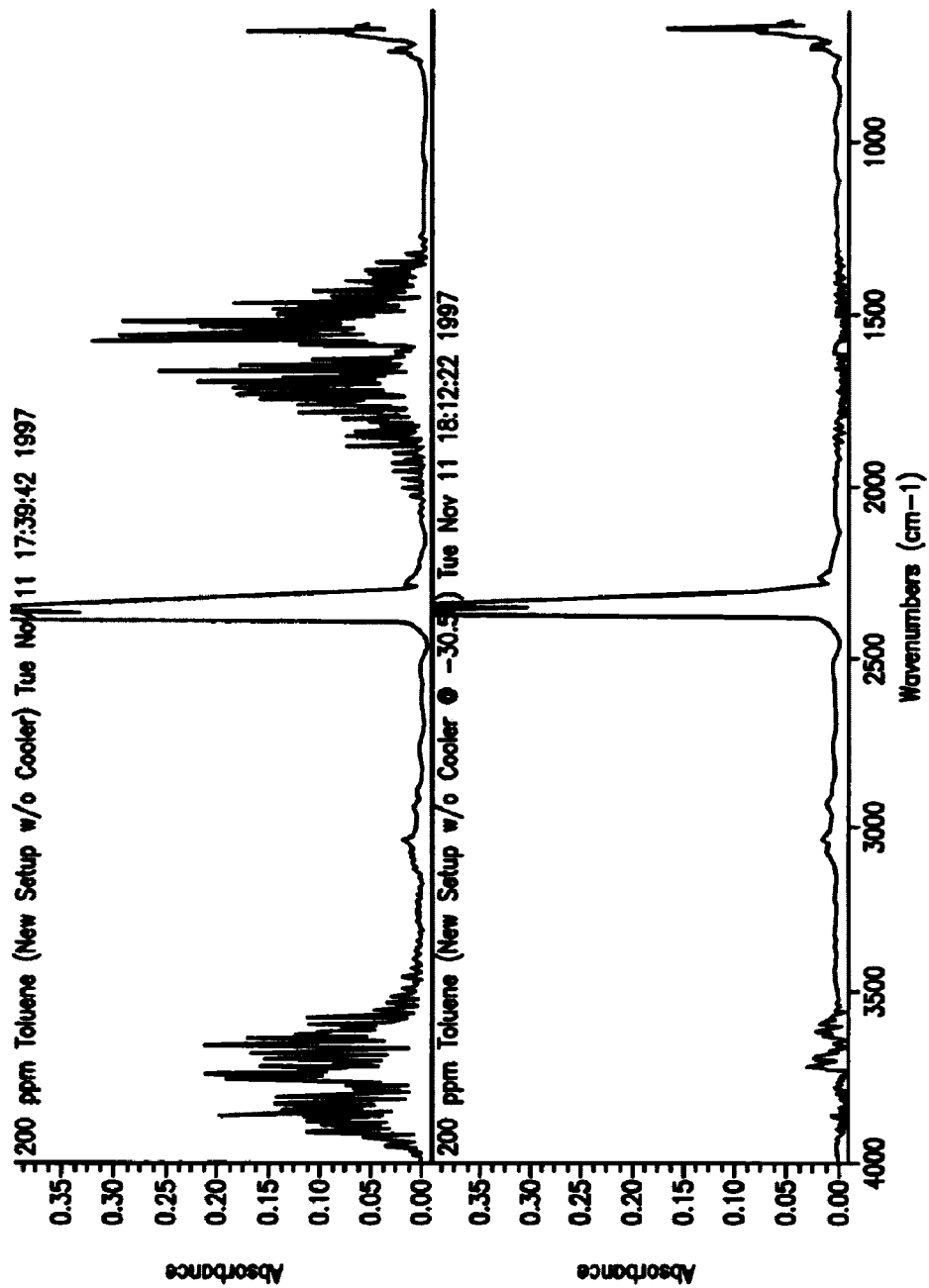
FIG. 8—infrared FTIR spectra for 200 ppm (volume) of toluene in room air (approximately 50% relative humidity), both with/without water trap filtration, showing water vapor reduction without significant organic compound loss. Spectrum shows the complete mid-infrared range.
Figure 9:
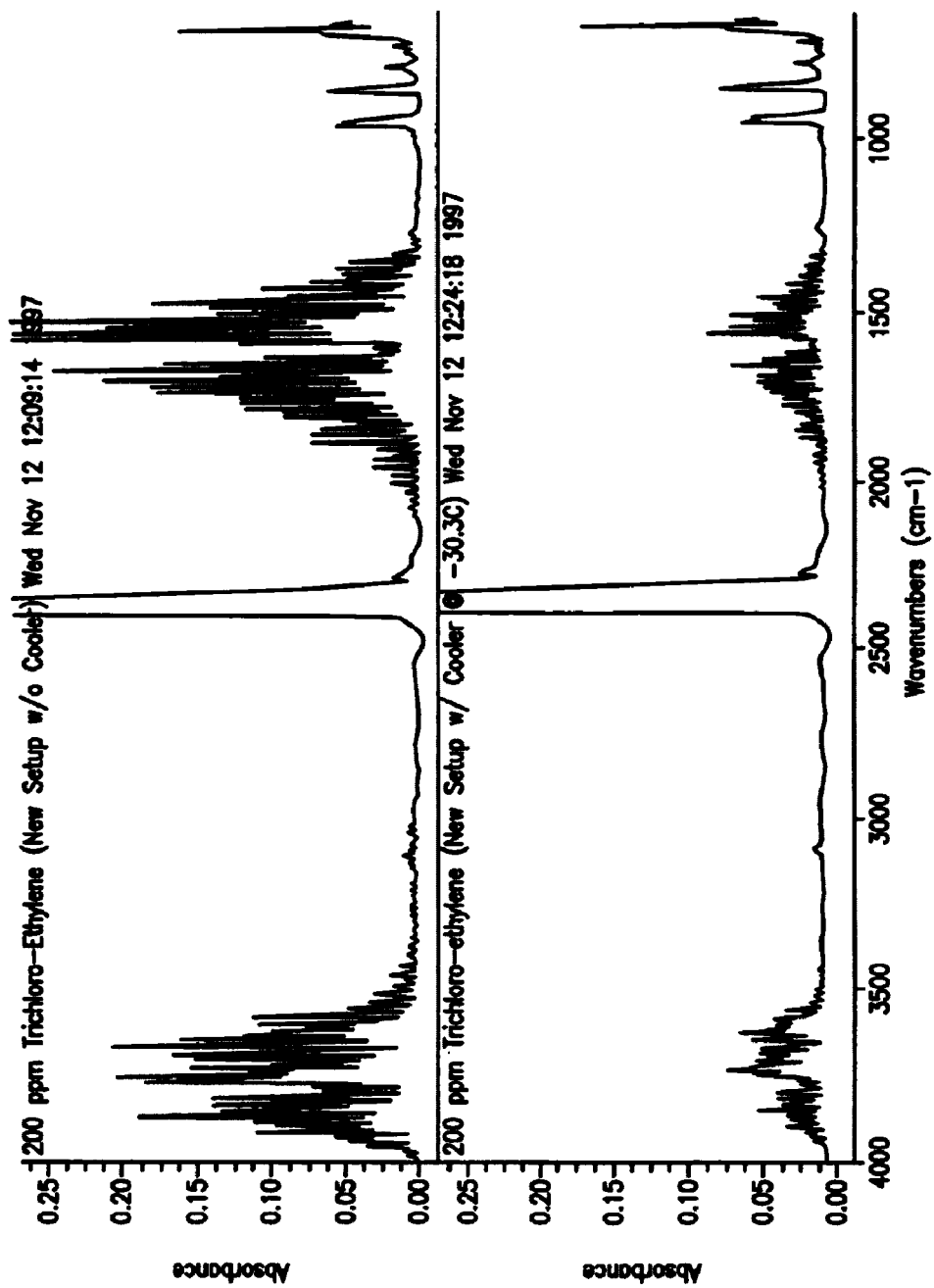
FIG. 9—infrared FTIR spectra for 200 ppm (volume) of trichloroethylene in room air (approximately 50% relative humidity), both with/without water trap filtration, showing water trap reduction without significant organic compound loss. Spectrum shows the complete mid-infrared range.
Figure 10:
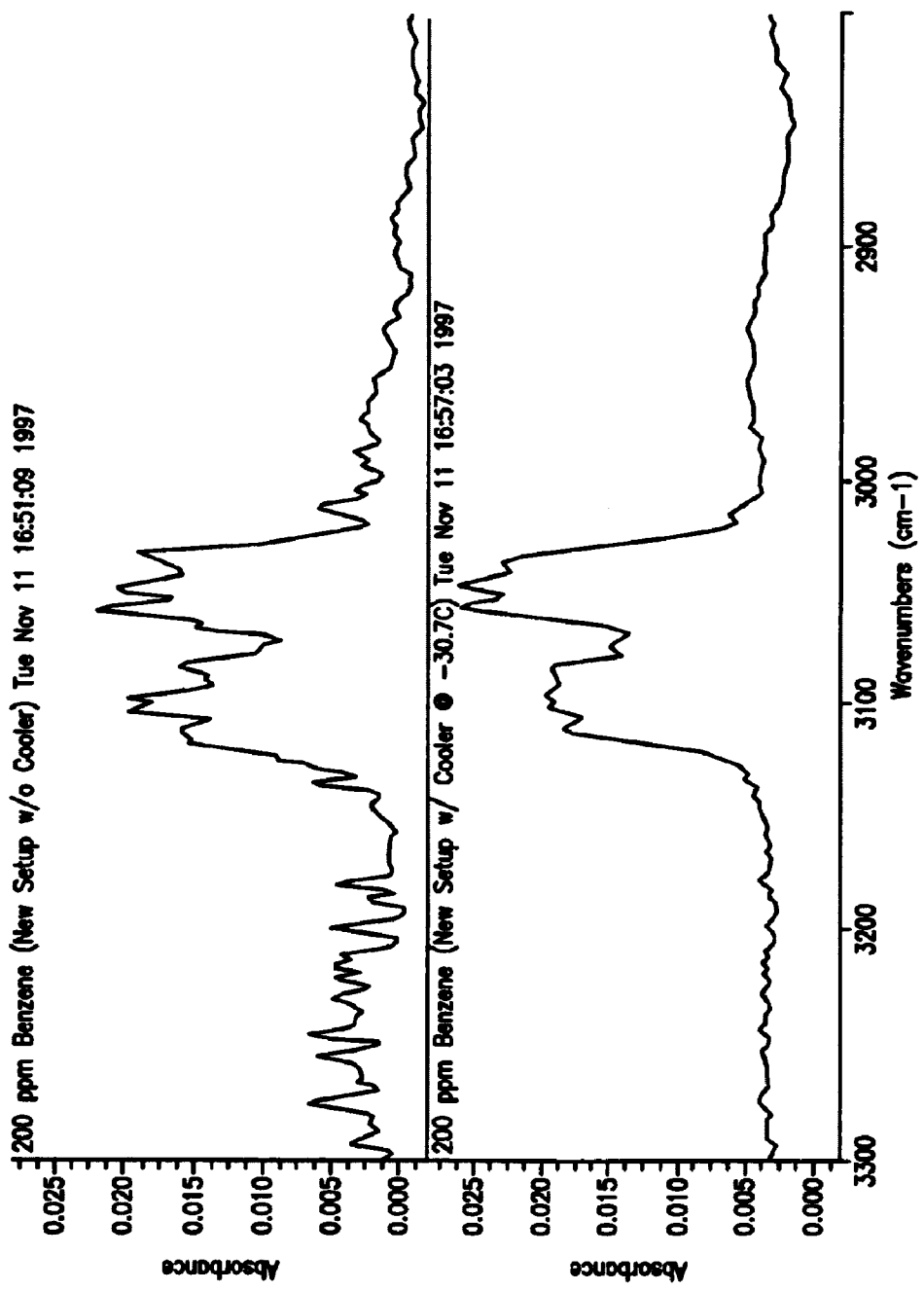
FIG. 10—infrared FTIR spectra for 200 ppm (volume) of benzene in room air (approximately 50% relative humidity), both with/without water trap filtration, showing water vapor reduction without significant organic compound loss. Spectrum shows the 3,330–2,800 $cm^{-1}$ region with strong hydrocarbon absorption bands.
Figure 11:
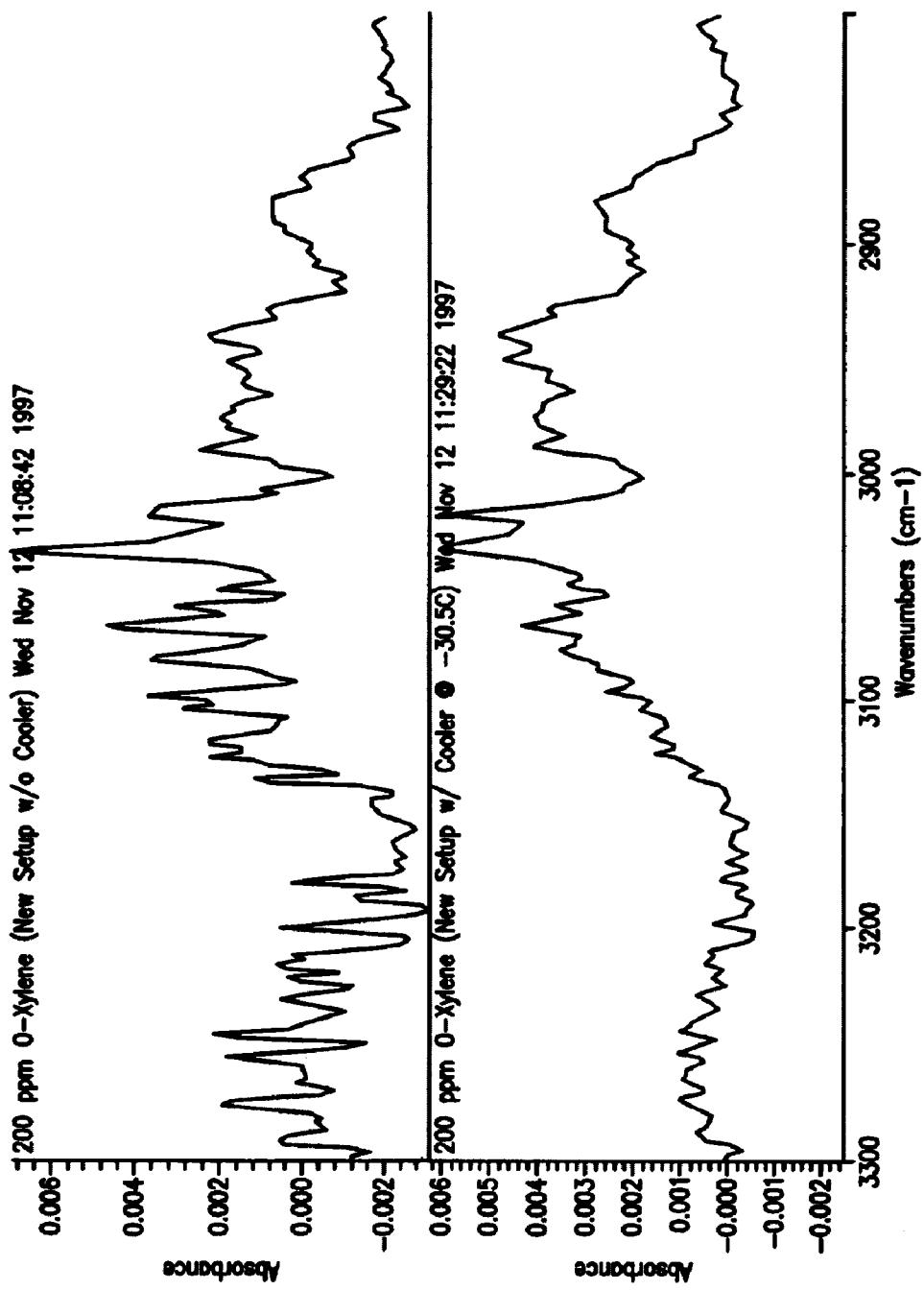
FIG. 11—infrared FTIR spectra for 200 ppm (volume) of o-xylene in room air (approximately 50% relative humidity), both with/without trap filtration, showing water vapor reduction without significant organic compound loss. Spectrum shows the 3,330–2,800 $cm^{-1}$ region with strong hydrocarbon absorption bands.
Figure 12:
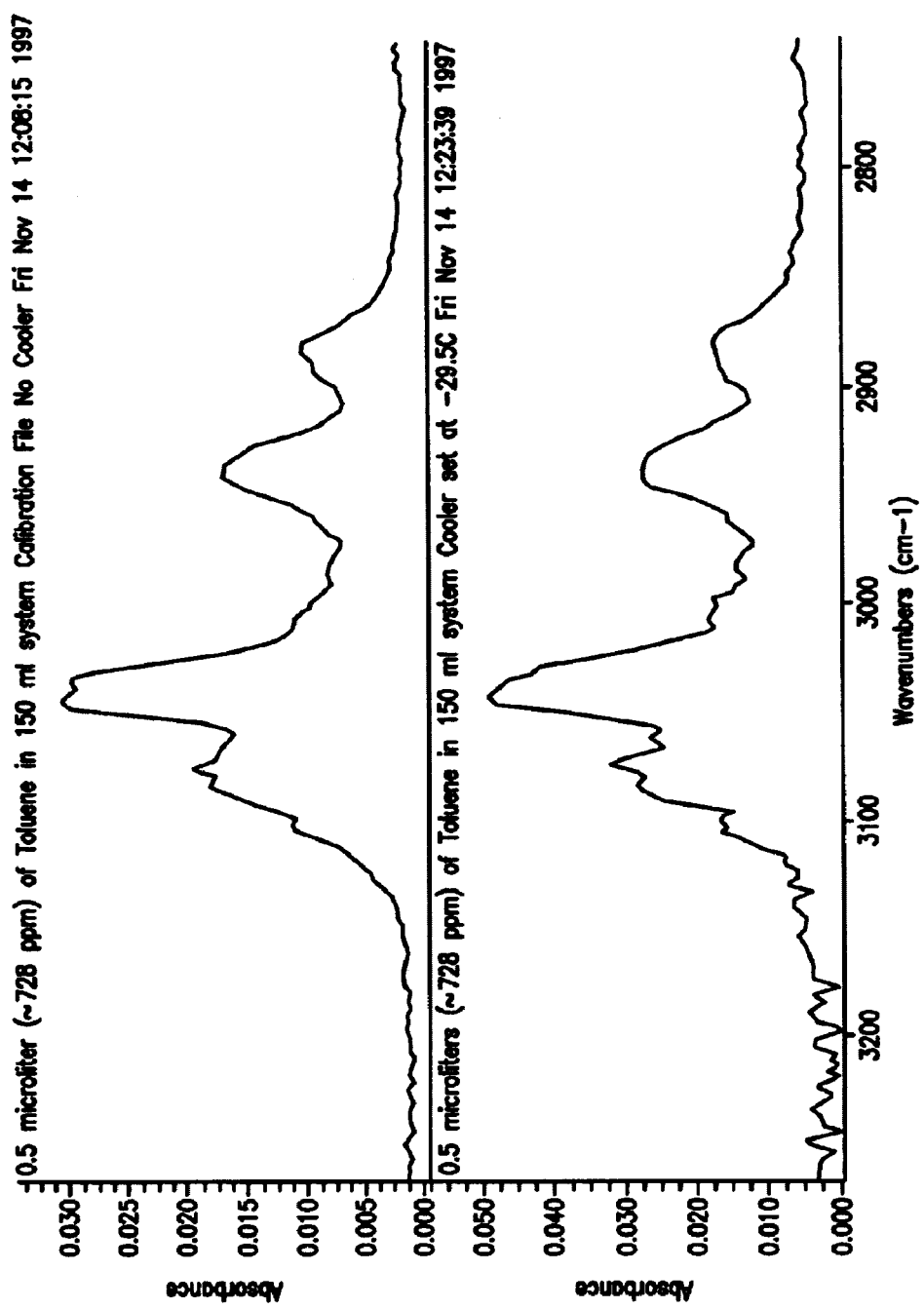
FIG. 12—infrared FTIR spectra for 200 ppm (volume) of toluene in room air (approximately 50% relative humidity), both with/without trap filtration, showing water vapor reduction without significant organic compound loss. Spectrum shows the 3,330–2,800 cm$^{-1}$ region with strong hydrocarbon absorption bands.
Figure 13:
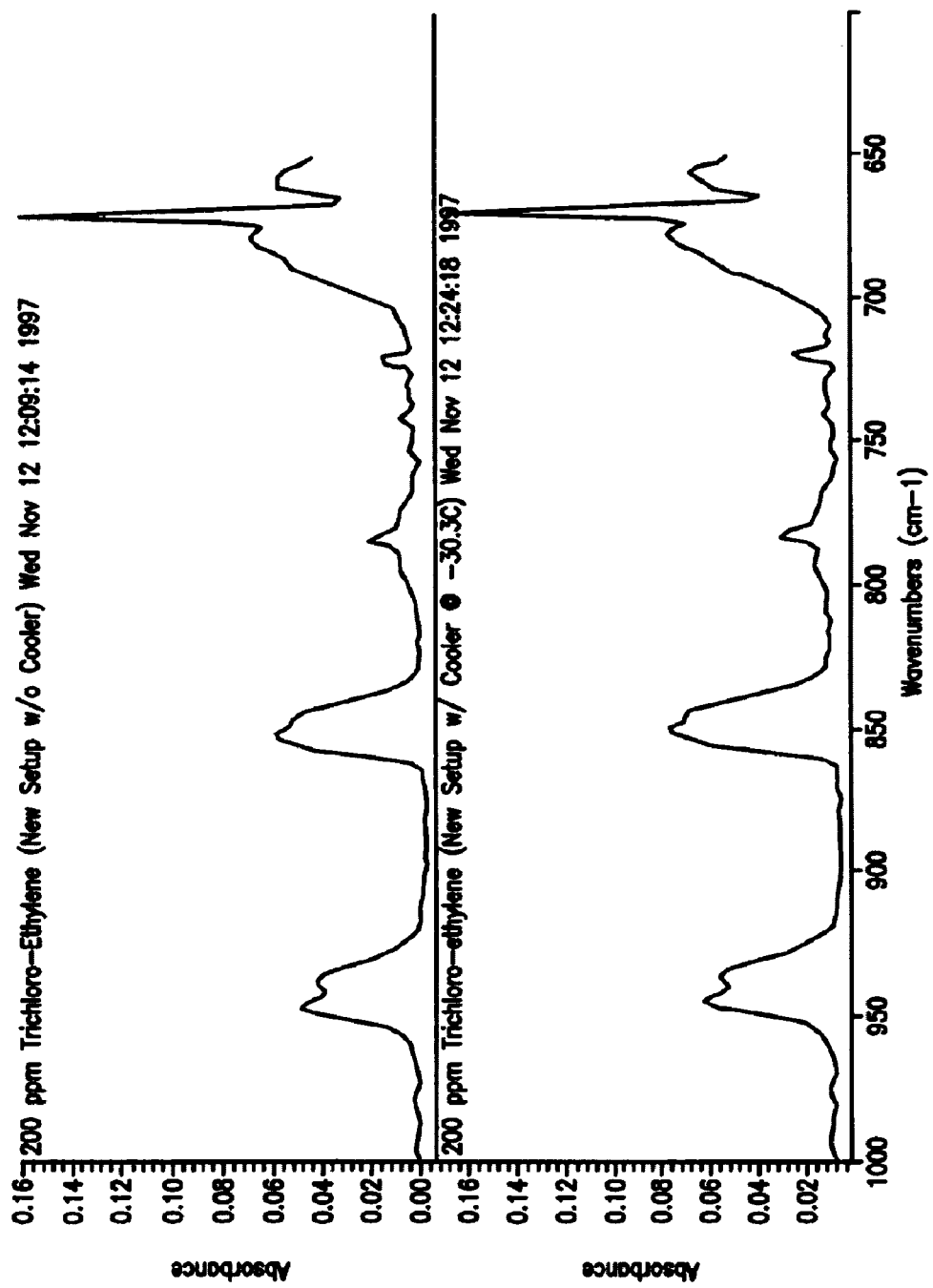
FIG. 13—infrared FTIR spectra for 200 ppm (volume) of trichloroethylene in room air (approximately 50% relative humidity), both with/without trap filtration showing water vapor reduction without significant organic compound loss. Spectrum shows the 3,330–2,800 cm$^{-1}$ region with strong hydrocarbon absorption bands.

The thermoelectrically cooled water trap 8 can be connected to an analytic device midline as shown in FIG. 4. FIG. 4 shows the present invention connected to a portable infrared spectroscopic gas analyzer for soil and water screening, but the present invention can be connected to any analytic device in which water vapor interference poses a problem. The inlet 3 and outlet ends 4 of the pipe 2 are used to connect the water trap to the system.

The water vapor laden sample air enters the inlet end 3 and exits with substantially less water vapor through the outlet end 4 and into the system for analysis. As shown in FIG. 4 an air pump or other similar functioning device should be used to push the sample air through the trap 8. It is important that the tube or other attachment apparatus of the system sealingly engages with the inlet 3 and outlet 4 ends of the pipe 2 to form an air tight seal. A tight seal is desired to prevent any sample air from escaping from the system. If necessary an adaptive device can be employed to ensure a seal.

Alternatively, the present invention can be attached to another type of analytic device at the front end of the system.

When attached to a system as described above a bypass line is used to allow analysis of air samples without passage through the water trap, when advantageous to do so.

Operation

In the illustrative examples the gas flow rate was held between 0.2 liters/min and 2.0 liters/min, however, the gas flow rate can be adjusted to suit the system in which the trap in employed. For example, in situations which require a single pass through the trap slower gas flow rates might prove beneficial as they allow the gas to spend more time within the heat exchanging pipe. It can be imagined that slower and faster flow rates might be used without departing from the spirit of the present invention.

The flow time is preferably sufficiently long for the gas to stay in the pipe 2 long enough to reach thermal equilibrium with the cool walls of the heat exchanging pipe 2. However, as mentioned earlier many gas monitoring applications require a measurement time of less than 2 minutes, which often makes reaching thermal equilibrium impossible. In any case the flow rate and flow time should be sufficient to allow the sample volume to pass through the trap at least once before being passed on for chemical anaylsis. The exact flow time and flow rate will depend on experimental conditions.

As noted earlier, the concentration of the trace components in the air sample are not usually reduced by the cold trap if the equilibrium vapor pressure of the compound are above their partial pressures in the air sample. Therefore it is preferable that the partial pressure of the compound being measured be at least 10 times lower than its equilibrium vapor pressure.

In some conditions certain compounds will be removed from the air sample even when their partial pressure are 10 times below their equilibrium vapor pressures. Therefore, it is preferable to keep the concentrations of the analyte elements/compounds below 200 ppm and more preferable to keep analyte concentration below 100 ppm.

In cases where the partial pressure of an analyte is too high to avoid partial pressure condensation, it may be necessary to dilute the gas sample in order to achieve such analyte concentrations. If one dilutes the sample, one can calculate actual concentration levels by multiplying the measured concentration by the amount of dilution as is well known in the art.

As shown in FIG. 1 the size of the present apparatus is very small, only being a few inches (1–10 inches) in length, height and depth. Although water traps of various sizes can be imagined, it is advantageous to have a small device that is both mobile and interchangeable with many systems.

Experimental Results

Figure 2:
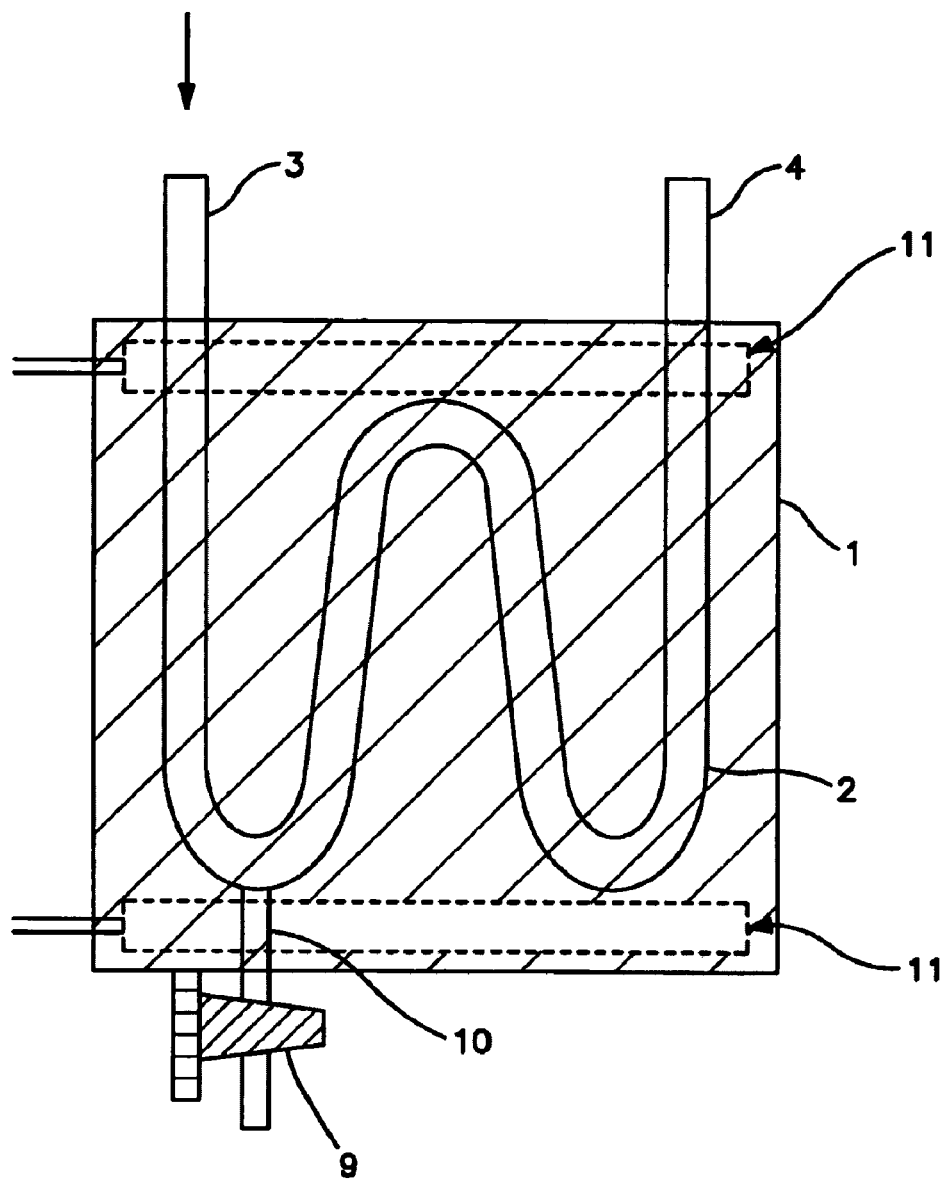
FIG. 2—is a cross sectional view of the copper metal plate; (expand)
Figure 3:
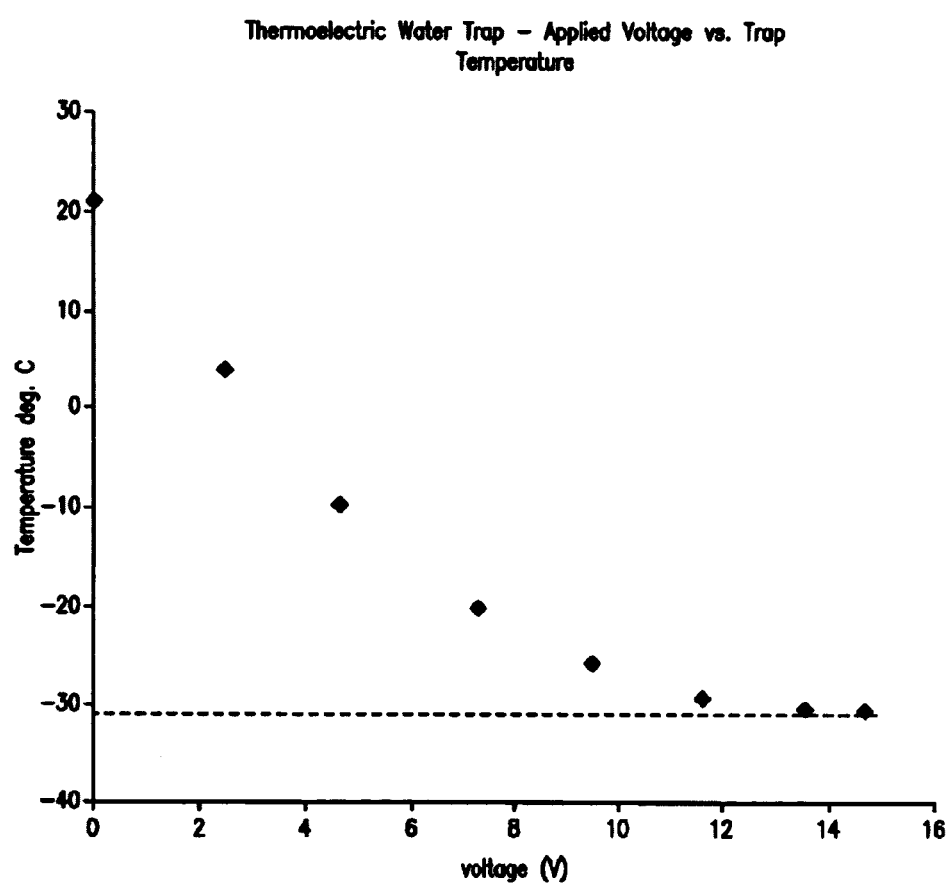
FIG. 3—is a plot of thermoelectric water trap gas line temperature v. voltage applied to the thermoelectric cooler.

In the following tests, a total gas sample volume of between 75 ml and 150 ml was passed through the water trap 8 with a gas flow rate of about 1,500 ml/min and a sample flush time of 10–30 seconds. The flow time was kept sufficiently long to allow the entire sample volume to pass through the trap at least twice. The measurements were made using Fourier Transform Infrared (FTIR) spectroscopy, having a 1 m pathlength waveguide gas cell to measure spectra. The cold trap 8 temperatures were held in the range of −28 to −30.7° C. The temperature of the trap 8 was measured with a thermocouple on the outside of the copper plate 1. The temperature of the outer surface of the plate 1 was found to correspond with the temperature inside the cooled heat exchanging tube 2 within 0.5° C. FIG. 2 shows a temperature v. supply voltage curve for the thermoelectric water trap as tested.

FIGS. 5–13 show FTIR spectra of four commonly used volatile solvents: benzene, o-xylene, toluene, and trichloroethylene, in humid air a concentration of 200 ppm (volume). In each case the spectra are shown with and without the application of the thermoelectrically cooled water trap 8 (trap temp at around −30° C.) to the gas sample before measurement. These spectra demonstrate a substantial reduction in the amount of water vapor in the sample as a result of application of the thermoelectrically cooled water trap 8.

FIGS. 10–13 show a sub-range within the full mid-infrared range to show that the water trap causes no significant loss in organic solvent concentration.

The thermoelectric water trap 8 as described is best suited for use in conjunction with a chemical analysis device or other apparatus. An example of two possible instrumental arrangements are shown in FIG. 4.

Alternate Embodiments

As described earlier, the water that is caught in the heat exchanging pipe 1 is present in the form of water droplets or condensed ice. The pipe 2 must be periodically flushed to remove this water and ice to ensure proper functioning of the trap 8. FIG. 2 shows an example of an alternate embodiment of the invention providing for this periodic removal of the condensed water/ice in the trap 8. The condensed water/ice is first converted to liquid by heating the trap to a temperature of 20–30° C. using two electrically powered heating elements 11 as shown in FIG. 2. In the illustrative embodiment heating elements manufactured from Minco Product Inc. (Minneapolis, Minn.) were used, but other heating elements with similar features could also be used.

Alternatively, one can use the Peltier device to heat the plate 1 and pipe 2 as Peltier devices work as heaters when current flow is reversed.

The liquid water condensate is purged from the copper gas tube through the drain valve 9 using pressurized air to flush out the system. The drain valve 9 is attached to the bottom of the plate 1 as shown in FIG. 2. A drain line 10 connects the inside of the pipe 2 with the valve 9 so that the water trapped in the pipe 2 can be flushed out. The drain line can be manufactured of any resilient material, preferably copper. The valve is a simple valve apparatus well known in the art. Additional condensate valves can be added at other points as needed.

The pressurized air is provided from a small portable air pump, a larger compressor system, a compressed air cylinder, or other source. The air is directed down the inlet 3 and/or outlet 4 ends of the pipe so that the water in the pipe 2 is forced out through the drain line 10 and drain valve 9. The pressurized air source may be pre-filtered with a chemical drying filter prior to entering the trap tube. The bulk of the condensed water will be located in the section of the tube between the inlet end and the first bend, and the water after becoming liquid will tend to collect at the lowest points of the pipe 2.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

All publications and patent documents cited in this application are incorporated by reference in their entirety for all purposes to the same extent as if each individual publication or patent document were so individually denoted

What is claimed is:

1. A thermoelectrically cooled water trap, comprising:
   a metal plate having a first side, a second side, top and a bottom, the metal plate further having a continuous cavity of specified shape, the cavity having a inlet end and outlet end which extend out of the plate's cavity;
   a metal pipe having a shape that is complementary to the shape of the metal plate's cavity, the metal pipe having an inlet end and an outlet end, the metal pipe being mounted within the metal plate's cavity, the length of the pipe being in physical contact with the plate with the exception of the inlet and outlet ends which extend out of the plate's cavity; and
   a thermoelectric cooler assembly having a first side and a second side, the first side of the cooler assembly being coupled to the first side of the metal plate; and
   an analytic measuring device, the analytic measuring device having a sample line, the sample line being connected to the inlet and outlet ends of water trap's pipe so that the sample passes through the water trap before being analyzed, the analytic device having a by-pass line that by-passes the water trap when desirous;
   wherein the temperature of the pipe is between −5° and −30° C. during normal operation.

2. A thermoelectrically cooled water trap as described in claim 1, further comprising a heat sink, the heat sink having a first side and a second side, the first side of the heat sink being in physical contact with and coupled to the second side of the cooler assembly.

3. A thermoelectrically cooled water trap as described in claim 2, wherein the second side of the heat sink has a series of fins which augment heat dispersal.

4. A thermoelectrically cooled water trap as described in claim 2, wherein the heat sink is aluminum.

5. A thermoelectrically cooled water trap as described in claim 2, wherein the first side of the heat sink is attached to the second side of the cooler assembly using fasteners.

6. A thermoelectrically cooled water trap as described in claim 2, further comprising a fan, the fan having a first and second side, the first side being coupled to the second side of the heat sink, the fan augmenting heat dispersal.

7. Thermoelectrically cooled water trap as described in claim 1, wherein the analytic measuring device is an infrared spectroscopic gas analyzer.

8. A thermoelectrically cooled water trap as described in claim 1, wherein the cavity of the metal plate has a shape with at least one bend, the shape allowing for a long pathlength through the plate.

9. A thermoelectrically cooled water trap as described in claim 1, wherein the metal pipe is w-shaped.

10. A thermoelectrically cooled water trap as described in claim 1, wherein the cavity originates at the top of the plate, winds through the central portion of the plate, and terminates at the top of the plate.

11. A thermoelectrically cooled water trap as described in claim 1, wherein the metal plate is manufactured of a metal having high-thermal conductivity.

12. A thermoelectrically cooled water trap as described in claim 1, wherein the metal plate is manufactured of copper.

13. A thermoelectrically cooled water trap as described in claim 1, wherein the metal pipe is manufactured of a metal having high thermal conductivity.

14. A thermoelectrically cooled water trap as described in claim 1, wherein the metal pipe is manufactured of copper.

15. A thermoelectrically cooled water trap as described in claim 1, wherein the pipe is coupled to the plate using Sb/Sn solder.

16. A thermoelectrically cooled water trap as described in claim 1, where the inlet and outlet ends of the pipe extend out of the plate a sufficient distance to allow connection of the ends to a tube.

17. A thermoelectrically cooled water trap as described in claim 1, wherein a thin coat of thermal interface material is applied to the first and second sides of the cooler assembly.

18. A thermoelectrically cooled water trap as described in claim 1, wherein the thermoelectric cooler assembly is a Peltier device.

19. A thermoelectrically cooled water trap as described in claim 1, wherein the first side of the cooler assembly is coupled to the first side of the plate using fasteners.

20. A thermoelectrically cooled water trap as described in claim 1, wherein the temperature of the pipe is lower than the dew point of the sample air.

21. A thermoelectrically cooled water trap as described in claim 1, wherein the temperature of the pipe is lower than room temperature, during normal operation.

22. A thermoelectrically cooled water trap as described in claim 1, wherein the analytic measuring device is used for infrared spectroscopy, mass spectrometry, ion mobility spectrometry or gas chromatography.

23. A thermoelectrically cooled water trap as described in claim 1, wherein the temperature of the pipe is between −5 and 10° C., during normal operation.

24. A thermoelectrically cooled water trap as described in claim 1, wherein the partial pressure of an analyte being measured is less than the equilibrium vapor pressure of the analyte.

25. A thermoelectrically cooled water trap as described in claim 1, wherein an analyte being measured has a concentration less than 200 ppm, by partial pressure.

26. A thermoelectrically cooled water trap as described in claim 1, wherein an analyte being measured has a concentration of less than 100 ppm, by partial pressure.

27. A thermoelectrically cooled water trap as described in claim 1, wherein the first side of the cooler assembly has a lower temperature than the second side of the assembly, during normal operation.

* * * * *